US009322805B2

(12) United States Patent
Koka et al.

(10) Patent No.: US 9,322,805 B2
(45) Date of Patent: Apr. 26, 2016

(54) LEAKAGE FLUX PROBE FOR NON-DESTRUCTIVE LEAKAGE FLUX-TESTING OF BODIES CONSISTING OF MAGNETISABLE MATERIAL

(75) Inventors: Ashraf Koka, Düsseldorf (DE); Alfred Graff, Essen (DE); Karsten Deegen, Düsseldorf (DE); Axel Heinz, Duisburg (DE)

(73) Assignee: Vallourec Deutshcland GmbH, Dusseldorf (DE)

( * ) Notice: Subject to any disclaimer, the term of this patent is extended or adjusted under 35 U.S.C. 154(b) by 353 days.

(21) Appl. No.: 13/402,012

(22) Filed: Feb. 22, 2012

(65) Prior Publication Data

US 2013/0057269 A1 Mar. 7, 2013

(30) Foreign Application Priority Data

Feb. 24, 2011 (DE) .......................... 10 2011 000 917

(51) Int. Cl.
  *G01N 27/82* (2006.01)
  *G01N 27/83* (2006.01)
(52) U.S. Cl.
  CPC ...................................... *G01N 27/83* (2013.01)
(58) Field of Classification Search
  CPC ............ G01N 27/90; G01B 7/34; G01R 33/12
  USPC ........................................................ 324/242
  See application file for complete search history.

(56) References Cited

U.S. PATENT DOCUMENTS

| | | | |
|---|---|---|---|
| 6,400,146 B1* | 6/2002 | Roy ............................... | 324/242 |
| 7,948,233 B2* | 5/2011 | Sheila-Vadde et al. ....... | 324/242 |
| 2007/0108971 A1* | 5/2007 | Dardik et al. .................. | 324/239 |
| 2008/0048646 A1 | 2/2008 | Wilkerson et al. | |
| 2009/0128152 A1 | 5/2009 | Dannels et al. | |
| 2012/0103097 A1* | 5/2012 | Lopez Jauregui ............... | 73/643 |
| 2012/0206132 A1* | 8/2012 | Lepage .......................... | 324/239 |

FOREIGN PATENT DOCUMENTS

| | | |
|---|---|---|
| CA | 2431008 C | 6/2002 |
| JP | 59202057 A | 4/1983 |
| JP | 07294490 A | 4/1994 |
| WO | 02/095383 A2 | 11/2002 |

* cited by examiner

*Primary Examiner* — Tung X Nguyen
*Assistant Examiner* — Feba Pothen
(74) *Attorney, Agent, or Firm* — Gardner, Linn, Burkhart & Flory, LLP

(57) ABSTRACT

A leakage flux probe for non-destructive leakage flux-testing of magnetizable bodies comprising a plurality of coils for detection of near-surface flaws in the body, wherein the coils have a degree of sensitivity which is dependent upon the orientation of the flaws in the body, and wherein coils having a different degree of sensitivity are disposed in the leakage flux probe with a first type of coil having a high degree of sensitivity for longitudinal flaws or transverse flaws and a second type of coil having a high degree of sensitivity for oblique flaws.

15 Claims, 3 Drawing Sheets

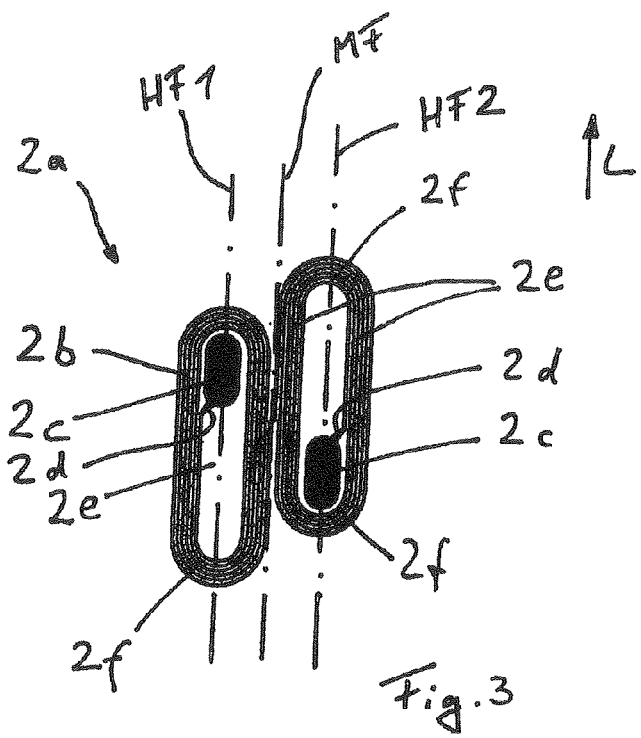
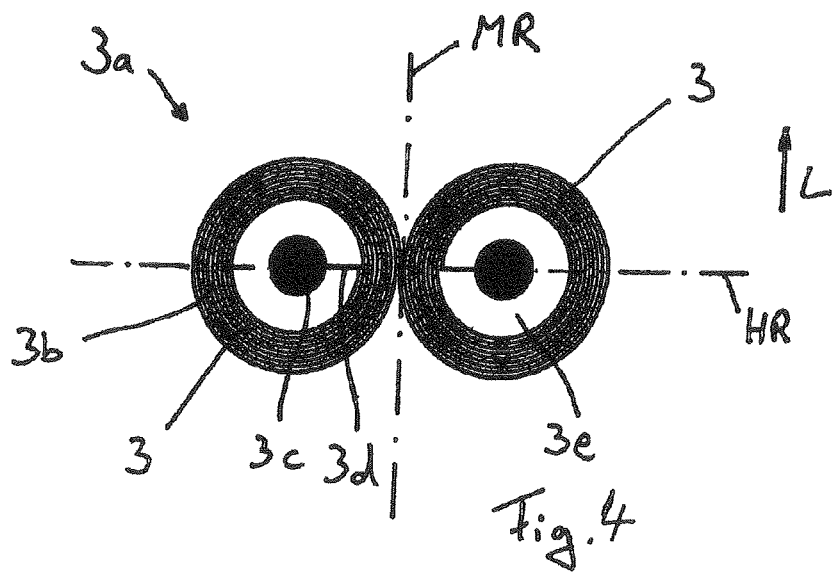

LEAKAGE FLUX PROBE FOR NON-DESTRUCTIVE LEAKAGE FLUX-TESTING OF BODIES CONSISTING OF MAGNETISABLE MATERIAL

BACKGROUND OF THE INVENTION

The present invention relates to a leakage flux probe for non-destructive leakage flux-testing of bodies consisting of magnetisable material, in particular of pipes consisting of ferromagnetic steel, having a plurality of coils for detection of near-surface flaws in the body, wherein the coils have a degree of sensitivity which is dependent upon the orientation of the flaws in the body.

For the purpose of non-destructive, near-surface testing of bodies consisting of magnetisable materials, it is generally known to use a so-called leakage flux method. For this purpose, the bodies which are to be tested are magnetised temporarily by electromagnets, cylinder coils or current linkage. In an homogeneous and flawless ferromagnetic material, the magnetic field lines are distributed uniformly over the surface. If the homogeneity of the material is disrupted by near-surface discontinuities, such as e.g. cracks, cavities, inclusions, pores or laminations, then magnetic field lines can emerge as so-called leakage flux from the workpiece in the region of the discontinuities. This leakage flux can be detected in a contacting or contactless manner by probes. A corresponding testing device typically includes a magnetisation unit, a handling unit for the body, a testing shoe having the leakage flux probes, an evaluating unit and optionally a demagnetisation unit. Current flux probes used for measuring the magnetic leakage flux density include induction probes, Giant-Magneto-Resistance probes (GMR-probes) or Hall-probes.

This known leakage flux-testing is also applied e.g. in the case of pipes consisting of ferromagnetic steel, in order to detect longitudinally and transversely oriented, as seen in the longitudinal direction of the pipes, and near-surface discontinuities on the inner and outer surfaces. In this case, unidirectional field magnetisation of the pipe is typically used, since flaws on the outer surface and on the inner surface of the pipe can be detected thereby. Alternating field magnetisation, which is used e.g. in the case of bar stock, can only detect flaws on the outer surface. In order to test the pipe for longitudinal flaws a magnetic field is applied at right angles and for transverse flaw testing a magnetic field is applied in parallel with the longitudinal axis of the pipe. In order to detect the entire surface when testing for longitudinal flaws in the pipe, the pipe and the probe are moved in helical fashion with respect to each other. Typically, when testing for transverse flaws, a probe having a probe ring is fixedly positioned around the pipe and serves to then move the pipe in the longitudinal direction. In order to calibrate the testing device, one or several grooves introduced onto a reference workpiece are used as a test flaw reference. The grooves simulate longitudinal, oblique and transverse flaws.

The German patent specification DE 198 23 453 C2 already discloses a leakage flux probe for non-destructive testing of elongate and rotationally symmetrical bodies, in particular pipes, for longitudinal or transverse flaws. The leakage flux probe consists substantially of a ruler-shaped printed circuit board, on whose side facing the body to be tested a plurality of coil pairs are printed. A total of 16 coil pairs are provided which as seen in the longitudinal direction of the printed circuit board are disposed in succession at a respectively identical spaced interval. Each individual coil of a coil pair comprises an elongate, substantially running track-like winding. Each winding is ring-shaped having a central longitudinal axis. The coils of a coil pair are each disposed slightly obliquely in relation to the longitudinal direction of the printed circuit board, so that in each case the longitudinal axis of the coils and the longitudinal direction of the printed circuit board form approximately an angle of 10 degrees. Moreover, as seen in the longitudinal direction of the printed circuit board, both coils or a pair are disposed laterally next to each other at a spaced interval and are offset with respect to each other in the longitudinal direction of the printed circuit board, so that as seen in the longitudinal direction of the printed circuit board the right-hand coil of a pair protrudes approximately two thirds of the length of the coil with respect to the left-hand coil. In this case, the coils of a pair are inclined to the right.

With the known leakage flux-testing, two mutually separate testing devices are used to reliably identify any longitudinal flaws in a first test and transverse flaws in a second test. Longitudinal and transverse flaw testing only identifies to a limited extent any oblique flaws extending obliquely with respect to the magnetic field direction.

Furthermore a sensor unit for magnetic testing of cracks is known from the Japanese laid-open document JP 59 202 057 A. The sensor unit consists of four sensors which are disposed one behind the other in series and are electrically connected in series. Each of the sensors is constructed in a manner comparable to a GMR-probe and their detection system is based upon magnetic resistance change. Moreover, each sensor consists of two first and second sensor parts which are disposed one behind the other in series and formed in each case in a meandering or comb-like manner. In this case, the tines of the comb of the first sensor part extend at a right angle to those of the second sensor part. Electrical contacts are provided between the first and second sensor parts and at the beginning and end of the sensor unit. This sensor unit is said to have the advantage that an adjustment of the amplification of the sensitivity for each sensor is to be avoided.

Furthermore, a further sensor unit for mechanical testing of cracks is known from the Japanese laid-open document JP 07 294 490 A, by means of which cracks extending in an oblique manner are to be identified in a particularly effective manner. For this purpose, a total of 16 sensors are provided which are disposed on a ruler-shaped holding element. In this case, two sensors in the form of a pair are each disposed next to each other and slightly offset with respect to each other as seen in the longitudinal direction of the holding element. Of these pairs, a total of 8 are disposed one behind the other as seen in the longitudinal direction of the holding element, which means that the arrangement of the sensors on the holding element can be described as being zigzag-like on the whole. In order to identify cracks, two of the sensors are each operated in a differential circuit. If a negatively oblique direction of the cracks is identified, two sensors which are disposed next to each other as seen in the longitudinal direction of the holding element are connected together in a differential circuit. In the event that a positively oblique direction of the cracks is detected, two sensors which are disposed one behind the other and next to each other as seen in the longitudinal direction of the holding element are connected together in a differential circuit. By virtue of this variable differential circuit, different sensors can be connected together in a differential circuit in dependence upon an orientation of a detected crack.

SUMMARY OF THE INVENTION

An object of the present invention is to provide a leakage flux probe for non-destructive leakage flux-testing of bodies consisting of magnetisable material, in particular of pipes consisting of ferromagnetic steel, which probe, in addition to the identification of longitudinal or transverse flaws, has an optimised degree of sensitivity in relation to the detection of oblique flaws.

This object is achieved by a leakage flux probe having, in one embodiment, a plurality of coils for detection of near-surface flaws in the body, wherein the coils have a degree of sensitivity which is dependent upon the orientation of the flaws in the body, and wherein coils having a different degree of sensitivity are disposed in the leakage flux probe with a first type of coil having a high degree of sensitivity for longitudinal flaws or transverse flaws and a second type of coil having a high degree of sensitivity for oblique flaws. Further advantageous embodiments of the invention are described herein.

In accordance with an aspect of the invention, in the case of a leakage flux probe for non-destructive leakage flux-testing of bodies consisting of magnetisable material, in particular of pipes consisting of ferromagnetic steel, having a plurality of coils for detection of near-surface flaws in the body, wherein the coils have a degree of sensitivity which is dependent upon the orientation of the flaws in the body, in addition to the identification of longitudinal flaws or transverse flaws, optimised sensitivity in relation to oblique flaws is achieved by virtue of the fact that coils having a different degree of sensitivity are disposed in the leakage flux probe and when testing for longitudinal flaws a first coil type has a high degree of sensitivity for longitudinal flaws and a second coil type has a high degree of sensitivity for oblique flaws. The invention serves to integrate reliable testing for oblique flaws into the testing of longitudinal flaws or transverse flaws. These previous tests for longitudinal or transverse flaws were not able to bridge the gap with respect to the detection of oblique flaws. The same can also be accomplished with respect to testing for transverse flaws.

The leakage flux probe in accordance with an embodiment of the invention is particularly suitable for testing for flaws in elongate and rotationally symmetrical bodies, in particular hot-rolled and seamless pipes. Flaws which are located on the outer or inner surface of the pipe can be caused by different factors. They can be caused e.g. by the preceding manufacturing steps (faulty inner tools or rollers) or by flaws in the basic material. The leakage flux probe in accordance with the invention renders it possible to localise and identify flaws at an early stage. As a consequence, in accordance with corresponding corrective measures high failure rates and post-processing rates can be obviated.

In particular embodiments the coils are formed as induction coils.

Testing for longitudinal and oblique flaws will be discussed hereinafter. In an advantageous embodiment it is provided that the coils are formed as imprinted flat coils which comprise either an elongate and annular winding (elongate annular coil) or a circular ring-shaped flat winding (circular coil). The elongate annular coils have a high degree of sensitivity for oblique flaws and the circular coils have a constant high degree of sensitivity for longitudinal and oblique flaws. By virtue of this innovative coil design, reliable testing for oblique flaws can also be incorporated into leakage flux-testing for longitudinal flaws. With regard to oblique flaws, the circular coils demonstrate a more balanced characteristic of the measurement values with respect to the elongate annular coils. In this case, the coils of one coil type are disposed next to one another in pairs and the coils of a pair are connected together. Reliable detection is achieved via a differential circuit of the coils. The different pairs of coil types are also disposed adjacent one another, in order thus to be able to detect longitudinal flaws and also oblique flaws in a reliable manner.

In particular embodiments it is provided that the longitudinal extension of the flat coils of a flat coil pair runs in parallel with a first centre line, the circular coils of a circular coil pair are oriented axis-symmetrically with respect to a second centre line and the first centre line is oriented at an angle of 30° to 45° with respect to the longitudinal extension of a longitudinal flaw and the second centre line is oriented at an angle of 40° to 60° with respect to the longitudinal extension of a longitudinal flaw. In a particular such embodiment, the first centre line is oriented at an angle of 40° with respect to the longitudinal extension of a longitudinal flaw and the second centre line is oriented at an angle of 53° with respect to the longitudinal extension of a longitudinal flaw. By virtue of these various selected geometries the sensitivity of the coils is adapted to longitudinal or oblique flaws. In a test on a pipe having artificial flaws in the form of grooves which each comprise angular positions of 0° to 90° offset by 5°, signal amplitude levels which have substantially constant values could be achieved over a broad range from 0° to approximately 50°. As a result, this leakage flux probe permits combined longitudinal and oblique flaw testing. In one embodiment, the two different coil types can be disposed alternately one behind the other. Therefore, a leakage flux probe having a larger detection range is provided.

Within the scope of non-destructive leakage flux-testing, a corresponding testing device comprises not only the leakage flux probe but also a magnetisation unit, by means of which the body for leakage flux-testing is magnetised by a magnetic field. In this case, it is provided in a particularly advantageous manner that the body is a pipe which for leakage flux-testing is magnetised by a unidirectional field and the magnetic field is oriented with its field lines perpendicular to any longitudinal flaws in the pipe. The advantage of unidirectional magnetisation resides in the fact that flaws on the outer surface and on the inner surface of the pipe can be detected thereby.

The invention will be explained in greater detail hereinafter with reference to an exemplified embodiment which is illustrated in the Figures.

BRIEF DESCRIPTION OF THE DRAWINGS

FIG. 3 shows an enlarged section of FIG. 2 from the region of a pair of flat coils, and FIG. 4 shows an enlarged section of FIG. 2 from the region of a pair of circular coils.

FIG. 1 illustrates a schematic view of a device for non-destructive leakage flux-testing of a hot-rolled seamless pipe 4 consisting of ferromagnetic steel for longitudinal flaws and oblique flaws. The pipe 4 typically comprises a central pipe axis R which extends in the longitudinal direction thereof. The core component of the testing device is a leakage flux probe which is part of a testing shoe 5. For testing purposes, the pipe 4 is moved in the feed direction V and the testing shoe 5 is moved in the circumferential direction U around the pipe 4, so that the pipe 4 is examined on a helical track. Testing for transverse flaws is performed by means of a further testing shoe, not illustrated, having a correspondingly adapted leakage flux probe. In this case, flaws are understood to be near-surface discontinuities, such as e.g. cracks, cavities, inclusions, pores or laminations. Typically, the testing shoe comprising the leakage flux probe is part of a testing device which also comprises a magnetisation unit, a handling unit for the pipe, an evaluation unit and a demagnetisation unit.

FIG. 2 illustrates a view of a printed circuit board 1 of a leakage flux probe. Of the printed circuit board 1 there is shown a view of so-called testing side 1a which faces towards the body which is to be tested—in this case the pipe. The printed circuit board 1 has an elongate and rectangular shape in the manner of a ruler with a longitudinal direction L pointing towards its longitudinal extension. Imprinted on the testing side 1a of the printed circuit board 1 are a plurality of coils which are formed as elongate annular coils 2 and as circular coils 3. The printed circuit board 1 has a width B which is selected such that as seen in the longitudinal direction L in each case two of the elongate annular coils 2 can be disposed next to one another in the form of an annular coil pair 2a and in each case two of the circular coils 3 can be disposed next to one another in the form of a circular coil pair 3a. Moreover, it is apparent from FIG. 1 that beginning with a first annular coil pair 2a, an annular coil pair 2a and a circular coil pair 3a are imprinted alternately one after the other in the longitudinal direction L of the printed circuit board 1. A total of eight annular coil pairs 2a and eight circular coil pairs 3a are provided.

Conductor tracks are imprinted on the rear side, which is not illustrated but is opposite the testing side 1a, of the printed circuit board 1, in order to connect the individual elongate annular coils 2 and the circular coils 3 electrically to a plug-in contact which is likewise attached to the rear side of the printed circuit board 1.

For the purpose of pipe testing, the printed circuit board 1 and thus the leakage flux probe is oriented with its longitudinal direction L in parallel with a longitudinally directed pipe axis R of the pipe. The pipe axis R runs centrally in the pipe and in the longitudinal direction thereof. Typically, longitudinal flaws F1 are understood to be flaws, whose longitudinal extension runs in parallel, i.e. at an angle of 0°, with respect to the pipe axis R. Consequently, transverse flaws F2 run at right angles, i.e. at an angle of 90°, with respect to the pipe axis R. Oblique flaws F3 are situated in the range between 0° to 90°. In relation to hot-rolled and seamless pipes, oblique flaws F3 with an orientation between 90° and 180° scarcely occur on account of the production method. In addition to the probe with the leakage flux probe, the testing device also includes the magnetisation unit for temporarily magnetising the pipe with a magnetic field M. In this case, the field lines of the magnetic field M run at right angles with respect to the pipe axis R, since in the present case the testing device is designed for identifying longitudinal flaws F1 and a broad range of oblique flaws F3.

Figure 1:
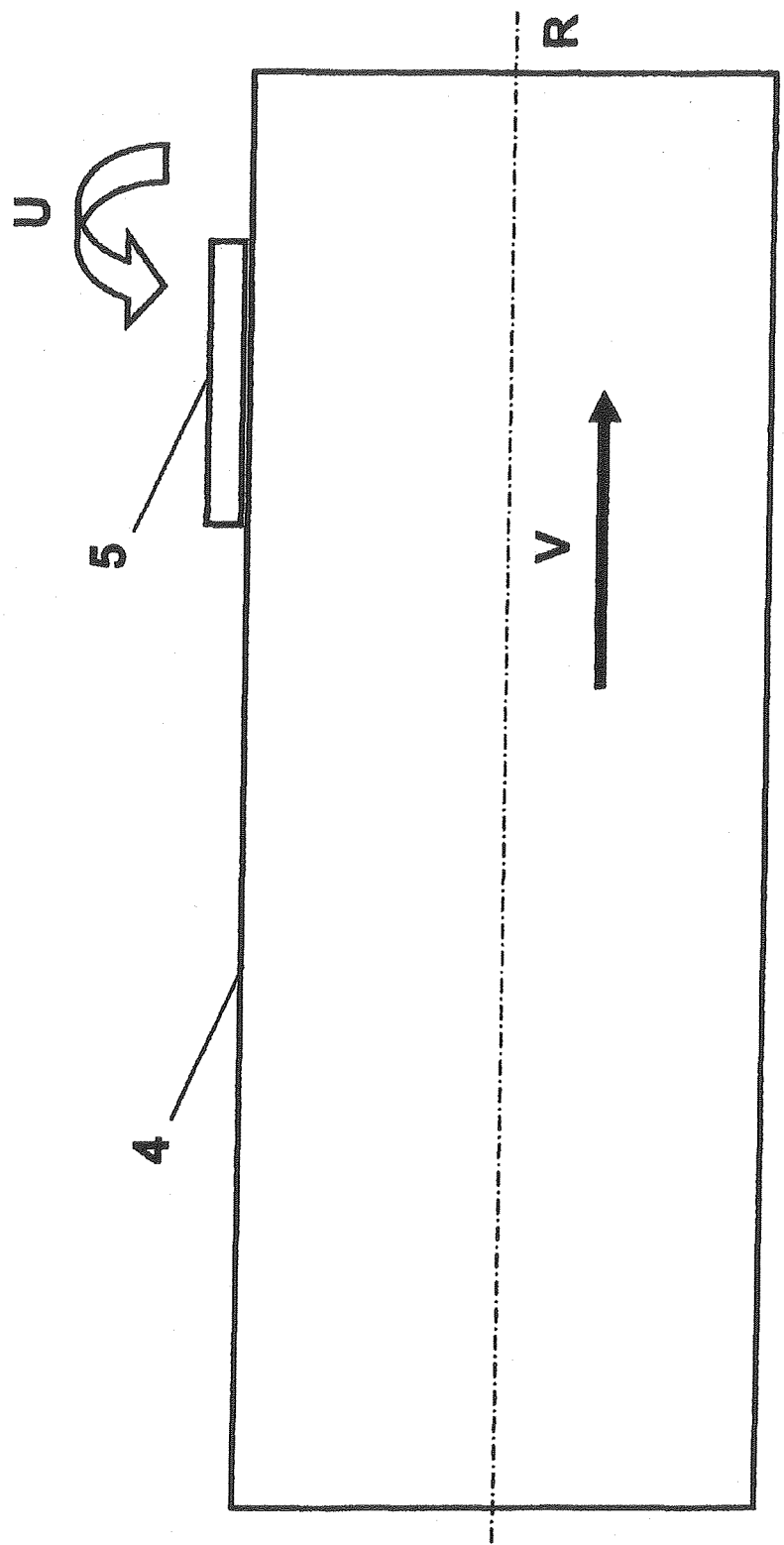
FIG. 1 shows a schematic view of a device for non-destructive leakage flux testing of pipes.

It is also apparent from FIG. 1 that although the annular coil pairs 2a and circular coil pairs 3a are located next to one another, they are oriented in a mutually offset manner in relation to the longitudinal direction L.

The annular coil pairs 2a consist in each case of two elongate annular coils 2 which each have the form of a running track and a length to width ratio of about 3:1. In order to be able to describe the position of the two elongate annular coils 2 within an elongate annular coil pair 2a, a first centre line MF is defined which runs in the centre between the two elongate annular coils 2 and runs in parallel with the longitudinal extension of each of the two elongate annular coils 2. The first angle a formed by the first centre line MF and the longitudinal extension L is in the range of 30° to 45° and is preferably 40°. Moreover, the two elongate annular coils 2 of an annular coil pair 2a are mutually offset in relation to the longitudinal direction L such that the elongate annular coils 2 are located with their curved sections approximately at a height in relation to the longitudinal direction L.

In contrast, the circular coil pairs 3a consist in each case of two circular coils 3 which have the form of a circular ring. In order to describe the orientation of the circular coils 3 of the circular coil pair 3a on the printed circuit board 1, an auxiliary line HR, which runs through the centre points of the two circular coils 3, and a second centre line MR which runs at a right angle thereto are defined. In this case, the second centre line MR runs in the centre between the two circular coils 3. The second angle b formed by the second centre line MR and the longitudinal direction L is in the range of 40° to 60° and is preferably 53°.

With the aid of this orientation of the elongate annular coils 2 and the circular coils 3 with respect to the pipe axis R, the leakage flux probe uses its annular coil pairs 2a and circular coil pairs 3a to scan a leakage flux, which is produced by any longitudinal and oblique flaws F1, F3, such that any longitudinal and oblique flaw is detected consecutively with respect to time by the two elongate annular coils 2 of the annular coil pair 2a and the two annular coils of the annular coil pair 3a. With the aid of the annular coil pairs 2a, the oblique flaws F3 are reliably identified in an angular range from 30° to about 70°. The annular coil pairs 3a reliably cover the longitudinal flaws F1 and the region of oblique flaws F3 in an angular range between 0° to about 40°. In a typically provided transverse flaw test, any remaining oblique flaws F3 in the range of greater than 60° are also identified. Therefore, the leakage flux probe in accordance with the invention can be used to bridge the gap of identifying oblique flaws in a combined two-stage longitudinal flaw and transverse flaw test.

In order to calibrate the testing device in accordance with the invention, one or several grooves, which are introduced onto a reference workpiece, are used as a test flaw reference. The grooves simulate longitudinal, oblique and transverse flaws. It is apparent that the amplitude level of the measurement signals in similar test flaws—such as in this case in the form of groves—which are situated in a different orientation with respect to the pipe axis R, the sensitivity of the coils 2, 3 depends upon the respective angular position of the grooves in the range of 0° to 90°. A change in the angular position by 5° can constitute a change in the amplitude level by 10-20%. Since the change in the amplitude level is a measure of the change in permeability and thus represents the relevance of a flaw or a discontinuity, the combination of elongate annular coils 2 and circular coils 3 permits a distinction to be made between discontinuities, which are not to be registered and are situated in a favourable orientation, with respect to relevant discontinuities with unfavourable angular positions.

Figure 2:
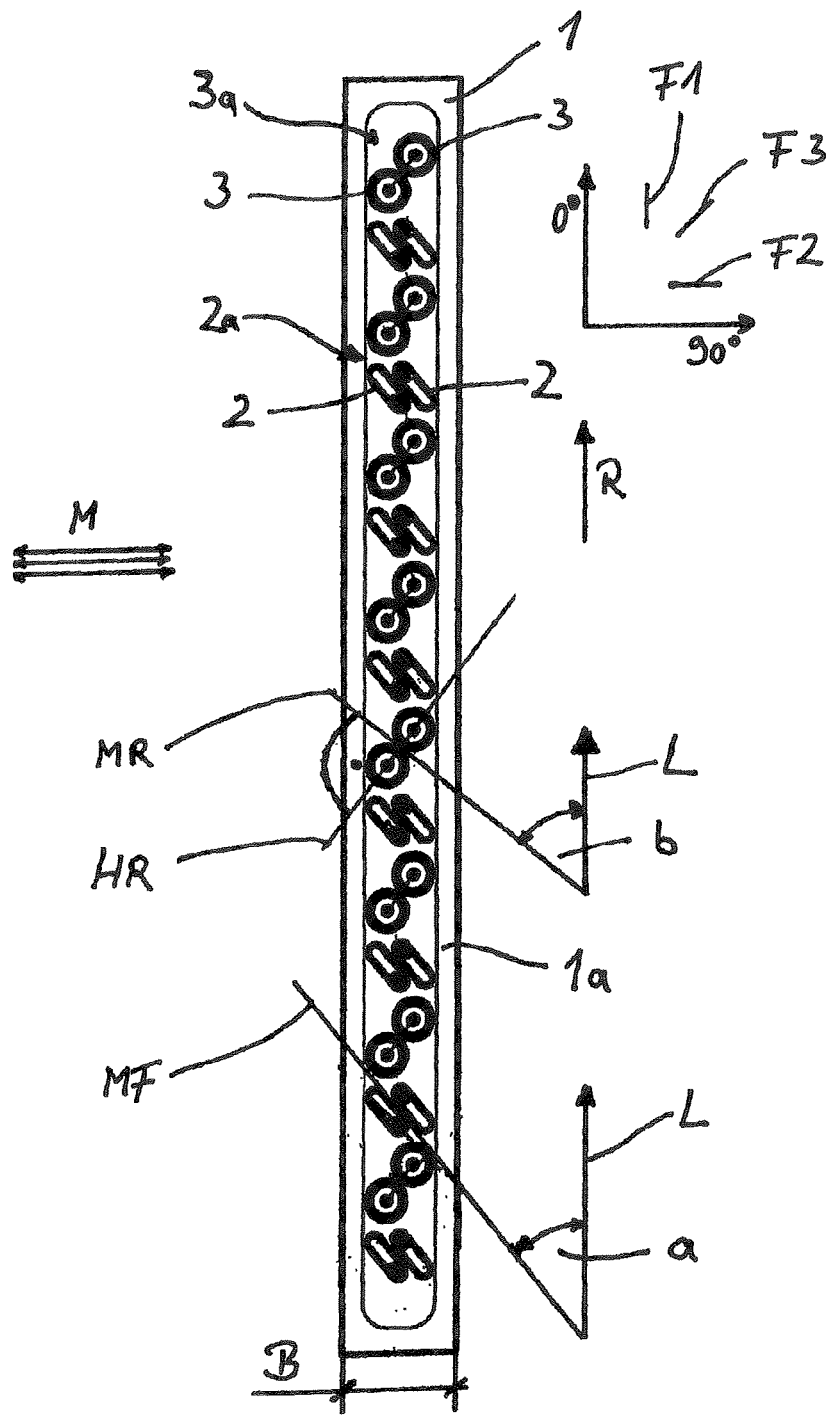
FIG. 2 shows a view of a printed circuit board of a leakage flux probe.

FIG. 3 illustrates an enlarged section of FIG. 2 from the region of an annular coil pair 2a of elongate annular coils 2. Each elongate annular coil 2 consists of an annular flat winding 2b which defines an inner space 2g. Disposed in each case in the inner space 2g is a contact surface 2c which is electrically connected in each case to a conductor track on the rear side of the printed circuit board 1. Starting from the left-hand contact surface of the two contact surfaces 2c, a winding conductor 2d runs in spiral fashion from the inside outwards, in order to form the flat winding 2b of the left-hand, elongate annular coil 2. In this case, the winding conductor extends in a running track-like manner through two parallel straight portions 2e which are opposite one another at a spaced interval and which are connected at their end regions via two 180°-curved sections 2f lying opposite one another at a spaced interval, in order to form the elongate shape of the elongate annular coil 2.

As already described, the annular coils 2 are formed in an elongate manner. Their longitudinal orientation can be defined by means of a second auxiliary line HF1, which runs through the apexes of the two 180°-curved sections 2f, for the left-hand, elongate annular coil 2, and a third auxiliary line HF2 for the right-hand, elongate annular coil 2. Since the two elongate annular coils 2, which are disposed next to one another, are oriented in parallel in relation to their longitudinal extension, the second auxiliary line HF1 and the third auxiliary line HF2 run in parallel with one another. A first centre line MR, which runs between the flat windings 2b of the right-hand and left-hand elongate annular coil 2 and by means of which the orientation of the elongate annular coil 2 can be defined, likewise runs in parallel with the second auxiliary line HF1 and the third auxiliary line HF2.

The elongate annular coils 2 of an annular coil pair 2a comprise a common winding conductor 2d and are thus connected in series. Accordingly, the flat winding 2b of the right-hand elongate annular coil 2 is also formed by the winding conductor 2d of the flat winding 2b of the left-hand elongate annular coil 2. For this purpose, the winding conductor 2d departs from the flat winding 2b of the left-hand elongate annular coil 2 into its outer region, is slightly offset in a lateral manner and then forms the winding region 2b of the right-hand elongate annular coil 2 in spiral fashion from the outside inwards. As seen from the inside outwards, the two flat windings 2b are wound anticlockwise. At the end of the winding region 2b of the right-hand elongate annular coil 2, the winding conductor 2d is connected to a right-hand contact surface 2c.

It is also apparent from FIG. 2 that although the right-hand and the left-hand elongate annular coils 2 are disposed next to one another, they are disposed slightly mutually offset in relation to the longitudinal direction L, so that in relation to the length of the elongate annular coil 2, the two elongate annular coils 2 are mutually offset approximately by one sixth of the length of one of the elongate annular coils 2. Consequently, in spite of the oblique orientation on the printed circuit board 1, the elongate annular coils 2 and circular coils 3 can be disposed closely one behind the other as seen in the longitudinal direction L.

FIG. 3 illustrates an enlarged section of FIG. 1 from the region of a pair 3a of circular coils 3. Each circular coil 3 consists of a circular flat winding 3b with an inner space 3e and a contact surface 3c which is disposed in the inner space 3e and is electrically connected to a conductor track on the rear side of the printed circuit board 1. Starting from the left-hand contact surface 3c, a winding conductor 3d runs in spiral fashion from the inside outwards, in order to form the flat winding 3b of the left-hand circular coil 3. The circular coils 3 of a circular coil pair 3a also comprise a common winding conductor 3d and are connected in series. Accordingly, the flat winding 3b of the right-hand circular coil 3 is also formed by the winding conductor 3d of the flat winding 3b of the left-hand circular coil 3. For this purpose, the winding conductor 3d departs from the flat winding 3b of the left-hand circular coil 3 into its outer region and then forms the winding region 3b of the right-hand circular coil 3 in spiral fashion from the outside inwards. As seen from the inside outwards, the two flat windings 3b are wound anticlockwise. At the end of the winding region 3b of the right-hand circular coil 3, the winding conductor 3d is connected to a right-hand contact surface 3c.

It is also illustrated in FIG. 1 that although the right-hand and left-hand circular coils 3 are disposed next to one another, they are disposed rotated about the common centre point in relation to a point on the longitudinal axis in the longitudinal direction L, so that in relation to the diameter of the circular coil 3 the two circular coils 3 are mutually offset approximately by three quarters of the diameter of the circular coil 3. Consequently, in spite of the oblique arrangement of the circular coils 3 on the printed circuit board 1, the elongate annular coils 2 and circular coils 3 can be disposed closely one behind the other as seen in the longitudinal direction L.

The present exemplified embodiment describes the probes as induction probes having elongate annular coils 2 and circular coils 3. In essence, it is also feasible to select different coil shapes. Other changes and modifications in the specifically described embodiments can be carried out without departing from the principles of the present invention, which is intended to be limited only by the scope of the appended claims, as interpreted according to the principles of patent law including the doctrine of equivalents.

LIST OF REFERENCE NUMERALS

1 printed circuit board
1a testing side
2 elongate annular coil
2a annular coil pair
2b flat winding
2c contact surfaces
2d winding conductor
2e straight portion
2f 180°-curved section
2g inner space
3 circular coil
3a circular coil pair
3b flat winding
3c contact surfaces
3d winding conductor
3e inner space
4 pipe
5 testing shoe
a first angle
b second angle
B width
F1 longitudinal flaws
F2 transverse flaws
F3 oblique flaws
HF1 second auxiliary line
HF2 third auxiliary line
HR first auxiliary line
M magnetic field
MF first centre line
MR second centre line
L longitudinal direction
R pipe axis

The invention claimed is:

1. A leakage flux probe for non-destructive leakage flux-testing of bodies comprising a magnetisable material, said leakage flux probe comprising a plurality of coils for detection of near-surface flaws in the body, wherein the coils have a degree of sensitivity which is dependent upon the orientation of the flaws in the body, and wherein coils having a different shape causing a different degree of sensitivity are disposed in the leakage flux probe with a first shape type of coil having a high degree of sensitivity for longitudinal flaws or transverse flaws and a second shape type of coil having a high degree of sensitivity for oblique flaws, wherein the first and second shape type of coils are annular and have an annular flat winding, the first shape type of coils is formed as circular coils, wherein the second shape type of coils is formed as elongate annular coils being a stretched circular coil, wherein the coils are imprinted on a testing side of a printed circuit board, the testing side facing towards the body to be tested.

2. The leakage flux probe of claim 1, wherein the coils are formed as induction coils.

3. The leakage flux probe of claim 1, wherein the coils of one sensitivity are disposed next to one another in pairs, and wherein the coils within one pair are connected differentially and the pairs of coils having different degrees of sensitivity are disposed adjacent one another.

4. The leakage flux probe of claim 3, wherein a longitudinal extension of the elongate annular coils of an annular coil pair runs in parallel with a first centre line and the circular coils of a circular coil pair are orientated axis-symmetrically with respect to a second centre line, and wherein the first centre line is oriented at an angle (a) of 30 degrees to 45 degrees with respect to the longitudinal extension of a longitudinal flaw and the second centre line is oriented at an angle (b) of 40 degrees to 60 degrees with respect to the longitudinal extension of a longitudinal flaw.

5. The leakage flux probe of claim 4, wherein the first centre line is oriented at an angle of 40 degrees with respect to the longitudinal extension of a longitudinal flaw and the second centre line is oriented at an angle of 53 degrees with respect to the longitudinal extension of a longitudinal flaw.

6. The leakage flux probe of claim 4, wherein the coils of one sensitivity and the coils having different degrees of sensitivity are disposed alternately one behind the other.

7. The leakage flux probe of claim 6 further including a magnetisation unit, said magnetisation unit being operable to provide a magnetic field to magnetise the body for leakage flux-testing.

8. The leakage flux probe of claim 7, wherein the body to be tested is a pipe which is magnetised by a unidirectional field for leakage flux-testing and the magnetic field is oriented with its field lines perpendicular to any longitudinal flaws in the pipe.

9. The leakage flux probe of claim 1, wherein a longitudinal extension of the elongate annular coils of an annular coil pair runs in parallel with a first centre line and the circular coils of a circular coil pair are orientated axis-symmetrically with respect to a second centre line, and wherein the first centre line is oriented at an angle (a) of 30 degrees to 45 degrees with respect to the longitudinal extension of a longitudinal flaw and the second centre line is oriented at an angle (b) of 40 degrees to 60 degrees with respect to the longitudinal extension of a longitudinal flaw.

10. The leakage flux probe of claim 2, wherein the coils of one sensitivity are disposed next to one another in pairs, and wherein the coils within one pair are connected differentially and the pairs of coils having different degrees of sensitivity are disposed adjacent one another.

11. The leakage flux probe of claim 10, wherein a longitudinal extension of the elongate annular coils of an annular coil pair runs in parallel with a first centre line and the circular coils of a circular coil pair are orientated axis-symmetrically with respect to a second centre line, and wherein the first centre line is oriented at an angle (a) of 30 degrees to 45 degrees with respect to the longitudinal extension of a longitudinal flaw and the second centre line is oriented at an angle (b) of 40 degrees to 60 degrees with respect to the longitudinal extension of a longitudinal flaw.

12. The leakage flux probe of claim 1, wherein the coils of one sensitivity and the coils having different degrees of sensitivity are disposed alternately one behind the other.

13. The leakage flux probe of claim 1 further including a magnetisation unit, said magnetisation unit being operable to provide a magnetic field to magnetise the body for leakage flux-testing.

14. The leakage flux probe of claim 13, wherein the body to be tested is a pipe which is magnetised by a unidirectional field for leakage flux-testing and the magnetic field is oriented with its field lines perpendicular to any longitudinal flaws in the pipe.

15. The leakage flux probe of claim 1, wherein the body to be tested is a pipe with a longitudinally directed pipe axis and the pipe axis is in parallel with a longitudinal direction of the circuit board.

* * * * *